(12) United States Patent
Wahl et al.

(10) Patent No.: US 6,295,680 B1
(45) Date of Patent: Oct. 2, 2001

(54) METHOD FOR DETECTING EARLY ATHEROSCLEROSIS AND VASCULAR DAMAGE USING RADIOACTIVE TRACERS AND INTRAVASCULAR RADIATION DETECTION DEVICES

(75) Inventors: Richard L. Wahl; Robert J. Lederman, both of Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/306,976

(22) Filed: May 7, 1999

(51) Int. Cl.[7] ........................................ A61B 5/00
(52) U.S. Cl. ........................................................ 14/1
(58) Field of Search ................................. 600/431, 436, 600/407, 1–8

(56) References Cited

U.S. PATENT DOCUMENTS

| | | | |
|---|---|---|---|
| 3,598,109 | * 8/1971 | Kobayashi et al. | 600/436 |
| 3,669,095 | * 6/1972 | Kobayashi et al. | 600/436 |
| 4,437,161 | * 3/1984 | Anderson | 78/98.12 |
| 4,660,563 | * 4/1987 | Lees | 424/1.69 |
| 5,166,073 | * 11/1992 | Lefkowitz et al. | 436/57 |
| 5,199,939 | * 4/1993 | Dake et al. | 600/3 |
| 5,203,338 | * 4/1993 | Jang | 128/662.06 |
| 5,453,575 | * 9/1995 | O'Dommell et al. | 128/662.06 |
| 5,558,093 | * 9/1996 | Pomeranz | 128/660.03 |
| 5,707,354 | * 1/1998 | Salmon et al. | 604/96 |
| 5,724,977 | * 3/1998 | Yock et al. | 600/437 |
| 5,811,814 | * 9/1998 | Leone et al. | 250/368 |
| 5,823,992 | * 10/1998 | Salmon et al. | 604/509 |
| 5,938,609 | * 8/1999 | Pomeranz | 600/439 |
| 6,026,317 | * 2/2000 | Verani | 600/420 |

\* cited by examiner

*Primary Examiner*—Teresa Walberg
*Assistant Examiner*—Daniel Robinson
(74) *Attorney, Agent, or Firm*—Harness, Dickey & Pierce, P.L.C.

(57) ABSTRACT

A method and apparatus for detecting and optionally treating metabolically unstable or active atherosclerotic plaque is provided. The patient is given an I.V. solution containing a radioactive tracer which specifically accumulates in these plaques. A miniaturized radiation detector for local radioactivity imaging and detection is applied directly within the arterial lumen. The radiation detector identifies and differentiates the active, unstable plaque from the inactive, stable plaque. Treatment may optionally be provided through any of three forms, including opening the vessel by mechanical expansion, removing the plaque by mechanical ablation, or delivering a metabolism-altering agent to the affected site.

14 Claims, 6 Drawing Sheets

METHOD FOR DETECTING EARLY ATHEROSCLEROSIS AND VASCULAR DAMAGE USING RADIOACTIVE TRACERS AND INTRAVASCULAR RADIATION DETECTION DEVICES

BACKGROUND OF THE INVENTION

1. Technical Field

The present invention relates generally to a method and apparatus for use in detecting focal accumulation of radiopharmaceutical agents within an arterial lumen. More particularly, the present invention provides a miniaturized fiber optic-coupled scintillator attached to an external image processing unit for detecting accumulated radiopharmaceutical agents within a blood vessel. Optionally, the apparatus may be fitted with a system for minimizing the accumulated plaque.

2. Summary of Related Art

Atherosclerosis is one of a handful of conditions in which a thickening or hardening of the walls of arterial vessels occurs, the other conditions being Monckeberg's sclerosis (deposition of calcium salts in the muscular wall of arteries) and arteriolosclerosis (thickening of arterioles). Atherosclerosis is generally multifocal. The lesion or atherosclerotic plaque—comprises a mass of fatty material. This material is associated with fibrous connective tissue and frequently includes deposits of calcium salts and other residual material. These plaques initially begin in the intima of the affected vessel but may eventually extend into the media of the vessel.

In developed countries, atherosclerosis is frequently seen in all but the youngest of people, although genetic predispositions play an important role in the course of the disease. The damage caused by atherosclerosis varies. If a medium-sized blood vessel such as a coronary artery is involved, the plaque build-up may restrict blood flow or may stop it altogether in more extreme cases. Thrombus formation may also result on the roughened area which results from the built-up plaques. Of considerable concern is the possibility of the soft lipid portion of the plaque breaking away and being deposited in a narrow vessel, frequently resulting in a stroke. Relief of focal high-grade obstruction may control symptoms, but the patient usually is left with numerous nonobstructive plaques prone to later rupture and infarction.

While conventional imaging and detection of coronary atherosclerosis by contrast angiography or intravascular ultrasonography provides valuable anatomic detail, it does not characterize the underlying biological processes which may lead to plaque expansion or rupture with attendant acute coronary syndromes. In particular, available imaging and detection modalities have limited ability to predict the site of future myocardial infarction and have demonstrated an inability to differentiate between active (unstable) and inactive (stable) plaque sites. While percutaneous coronary revascularization provides excellent symptom relief in selected patients with obstructive coronary artery disease, it has been difficult to demonstrate that percutaneous revascularization reduces the incidence of future myocardial infarction.

While all plaque build-up on vessel walls is to be of concern, it is impractical to resolve each plaque site throughout the affected individual's vascular system. Atherosclerotic plaques are characterized by mural inflammatory infiltrates which may contribute to their instability. Noninvasive imaging and detection of mural inflammation in atherosclerotic arteries is hampered by small tissue mass, high background activity from visceral and blood pool radiotracer, poor spatial resolution, poor correlation with local anatomy, and, in coronary arteries, by cardiac motion artifact. It is accordingly desirable to treat the most potentially dangerous plaques, or the so-called "active" plaques which are metabolically active. It is this form of plaque that cause the most trouble to the body in the form of coronary artery disease and atherosclerosis because of their tendency to let loose some of the lipid material from the site causing thrombosis. If loosened, this material could travel through the vascular system causing a coronary attack if in the region of the heart, a stroke if in the region of the brain, or an occlusion of a vessel if in the leg. The difficulty is in identifying the stable plaque from the unstable plaque and providing a method of treatment.

Accordingly, a method to identify the active, unstable, or "vulnerable" coronary atherosclerotic plaques might have broad clinical utility and remains wanting in the art.

SUMMARY OF THE INVENTION

It is accordingly an object of the present invention to provide a method and apparatus capable of differentiating active (or unstable) plaque from inactive (or stable) plaque.

It is a further object of the present invention to provide such a method and apparatus which is minimally invasive.

Yet a further object of the present invention is to provide such a method and apparatus which may optionally treat the identified and affected site.

Still a further object of the present invention is to provide such a method and apparatus which treats the affected site by expansion through the use of a balloon or a stent.

An additional object of the present invention is to provide such a method and apparatus which treats the affected site by mechanical means such as ablation through mechanical cutting or laser cutting.

A further object of the present invention is to provide such a method and apparatus which treats the affected site by treatment directed at altering metabolic activity.

These objects are accomplished through the provision of a miniaturized radiation detector for local radioactivity imaging and detection applied directly within the arterial lumen. Local imaging and detection isolates a small volume of interest from a larger pool of background radioactivity. Furthermore, a suitable intravascular device may be insensitive to cardiac motion, have a clinically-useful spatial resolution using several available clinical radionuclides, and may correlate images in real-time with conventional coronary or peripheral cineangiograms.

The apparatus and method of the present invention may be widely applicable in the study, diagnosis, and management of coronary and non-coronary atherosclerosis by tracing in vivo biochemical processes using radioactive tags. The method and apparatus of the present invention may be used to detect processes not otherwise amenable to study using conventional techniques including contrast angiography and intravascular ultrasound. The local-imaging and detection approach is superior to conventional radiopharmaceutical imaging and detection with external gamma or positron tomography systems.

The method and apparatus of the present invention overcomes many of the problems generally associated with external imaging and detection strategies which are limited by the low volume of pathological tissue, low signal-to-noise ratios from low lesion radioactivity and high background activity from blood pool and viscera. External imaging and detection is also limited by poor spatial resolution, poor correlation with local anatomy, and cardiac motion artifact. Conversely, the present method and apparatus provides a miniaturized radiation detector which identifies local radioactivity imaging and detection directly within the coronary artery lumen. Local imaging and detection isolates a small volume of interest from a larger pool of background radioactivity. In addition, the apparatus of the present invention is sensitive to cardiac motion, demonstrates clinically-useful spatial resolution using most clinical radionuclides, and is able to correlate images in real-time with conventional cineangiograms. Furthermore, the radiation detector material is especially suited for detecting beta particles (electrons and positrons, which have tissue penetrance limited to several millimeters), making this device particularly suitable for intravascular applications.

More particularly, the apparatus of the present invention is an ultraminiaturized device which embodies the properties of intracoronary devices including flexibility (the ability to travel around a bend with a narrow radius), softness (the ability to travel around a bend without straightening a vessel and without damaging its endoluminal surface), traceability (the ability to navigate a tortuous vessel), pushability (the ability to translate axially along an endoluminal guidewire). In addition, the apparatus of the present invention provides signal transmission at-a-distance between the intravascular target (access percutaneously) and the external instrumentation.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which.

DETAILED DESCRIPTION OF THE PREFERRED EMBODIMENT

The drawings disclose the preferred embodiment of the present invention. While the configurations according to the illustrated embodiment are preferred, it is envisioned that alternate configurations of the present invention may be adopted without deviating from the invention as portrayed. The preferred embodiment is discussed hereafter.

The method and apparatus of the present invention may be theoretically used for detecting and, optionally, treating almost any vessel having sufficient size to accommodate the detector (the catheter) itself. Conceptually this could be the heart and its proximal vessels such as the aorta, but the present invention would most likely find application in peripheral arteries which are larger such as the types that you would find in the patient's leg. Ideally the method and apparatus could be used to investigate and possibly treat the coronary artery or one or both of the carotid arteries.

Figure 1:
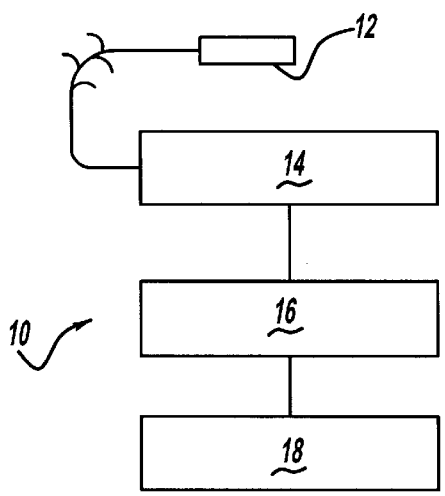
FIG. 1 is a diagrammatic view of the overall system of the present invention.

A diagrammatic view of the apparatus for use in the present method is illustrated in FIG. 1. The apparatus is generally illustrated as 10 and includes a detection and signal-producing sensor (or catheter) 12 for insertion into a blood vessel, an analyzer 14 to analyze the signal outputted from the catheter 12, an amplifier 16 to amplify the analyzed signal outputted from the analyzer 14, and an information output component 18 to visually display or print out the information received from the amplifier 16. In a preferred embodiment, the catheter 12 may be connected to a photomultiplier.

Figure 2:
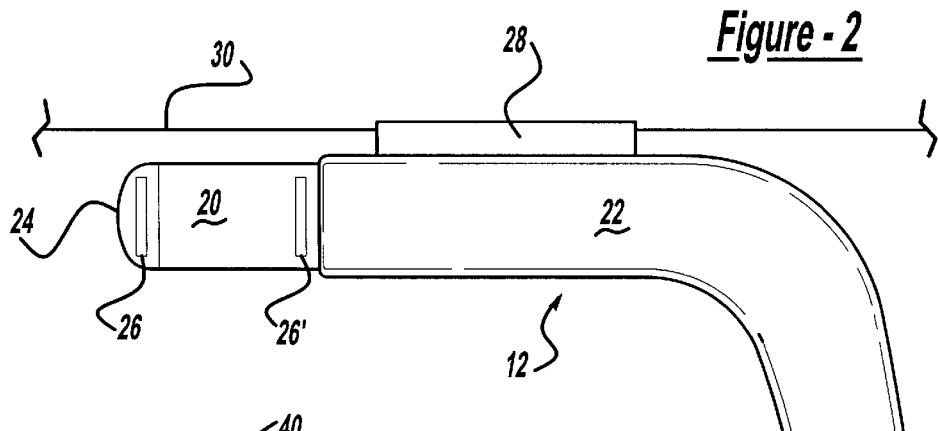
FIG. 2 is a perspective view of a preferred embodiment of the catheter according to the present invention.

FIG. 2 is a perspective view of a preferred embodiment of the catheter 12 according to the present invention. The catheter 12 basically includes a (plastic) scintillator 20 and a fiber optic cable 22. The scintillator 20 includes a blunt nosecone 24 and a pair of radiopaque geometry markers 26, 26'. A guidewire sleeve 28 slidably attaches the catheter 12 to a guidewire 30. As is known in the art, the guidewire 30 provides a track upon which the catheter 12 travels through the involved vessel to its destination. The scintillator 20 is integrated within the catheter 12 and is designed to navigate tortuous arterial segments, particularly within coronary arteries.

While the catheter 12 for use in the present invention has been described as being composed of a plastic scintillator 20 in conjunction with a fiber optic cable 22, it must be understood that alternate catheter constructions and systems may be used. In operation, the patient is given an I.V. solution containing a radioactive tracer such as 18-FDG (fluorodeoxyglucose; other tracers may be used as discussed below). The selected radioactive tracer would specifically accumulate in the metabolically unstable (or active) plaques. The area of tracer concentration would thus demonstrate a higher level of radioactivity than the surrounding area which, because of its lack of metabolic activity, would not accumulate tracer.

Figure 3:
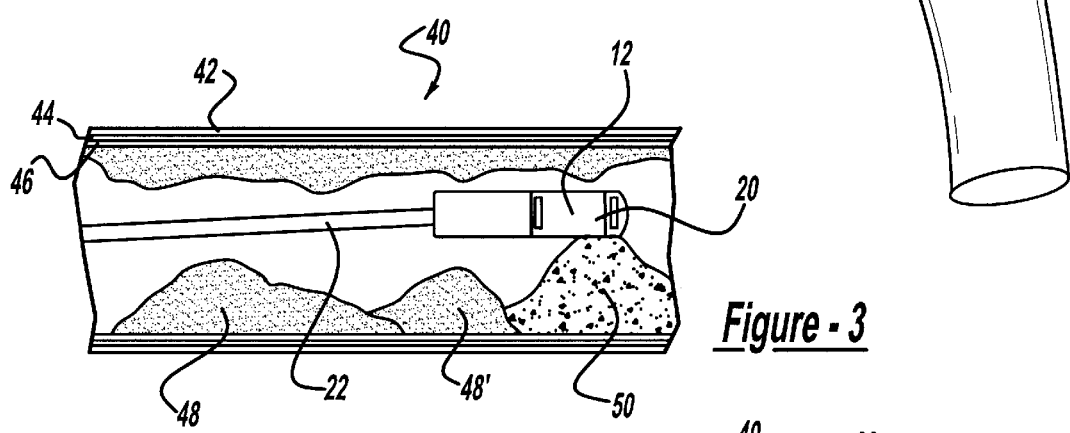
FIG. 3 is a sectional view of a blood vessel demonstrating atherosclerotic plaque buildup and the preferred embodiment of the catheter of the present invention situated within the blood vessel.

After a selected amount of time (for example, 2 to 4 hours, although this amount of time could be varied) the guide wire 30 of the catheter 12 is initially placed into the patient's body through a suitable insertion point such as the iliac artery. The guide wire 30 is inserted to a length that is adequate to provide a guide for the catheter 12 to the desired point of investigation and, optionally, treatment. The catheter 12 is then inserted and follows along the guide wire beyond the estimated site of occlusion, such as that illustrated in FIG. 3, which illustrates a sectional view of a blood vessel, generally illustrated as 40. The vessel 40 includes an outer layer 42 (tunica adventitia), a middle layer 44 (tunica media), and an inner layer 46 (tunica intima). Formed on the inner layer 46 are plaque deposits of which deposits 48, 48' are inactive, stable deposits and deposit 50 is an active, unstable deposit. (As illustrated, the catheter 12 has identified the active, unstable area 50 and is proximate thereto.)

Following extreme insertion, the catheter 12 is then slowly withdrawn to a certain point and a reading is made.

The catheter 12 is then withdrawn by an additional incremental amount, and a second reading is made. Withdrawal of the catheter 12 is slowly effected and readings are made along the course.

At some point there would be a high signal produced by the information output component 18 which would indicate an area of relatively high metabolic activity. (The high signal would be very high compared with the background, and experimental investigation indicates that the ratio of abnormal-to-normal activity could be 3:1 or greater.) The high signal identifies the target area of metabolic activity and instability.

Once identification is made, treatment would follow. A desired optional feature of the apparatus of the present invention would be to provide the catheter or detecting device with a mechanism for affecting treatment. Treatment may be in any of three forms, including opening the vessel by mechanical expansion, removing the plaque by mechanical ablation, or delivering a metabolism-altering agent to the affected site.

Figure 4:
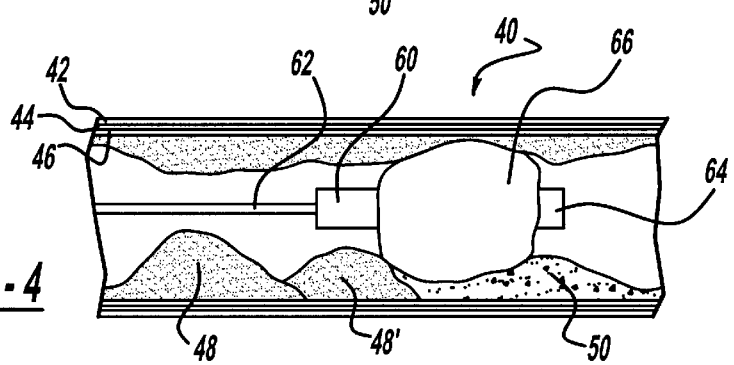
FIG. 4 is a sectional view of a blood vessel similar to that shown in FIG. 3 but illustrating an alternate embodiment of the catheter of the present invention.

With respect to the first possible mode of treatment, that of mechanical expansion, this may be accomplished by a combined detector-expander apparatus. Such an apparatus might include a detector combined with a balloon capable of performing an angioplasty of the site. FIG. 4 illustrates a sectional view of the blood vessel 40 which includes the inactive, stable plaque deposits 48, 48' the active, unstable plaque deposit 50. A combined balloon-sensor 60 is illustrated and includes a cable 62, a detector portion 64, and a balloon 66.

An alternative mechanical expansion mechanism (not shown) includes a detector that is combined with an expandable stent for installation at the affected site.

With respect to the second possible mode of treatment, that of mechanical ablation to perform an atherectomy, the detector may be fitted with a cutting or scraping device (such as blade or a series of blades or a laser device; not shown) which would remove the active plaque which may be later withdrawn by suction.

Figure 5:
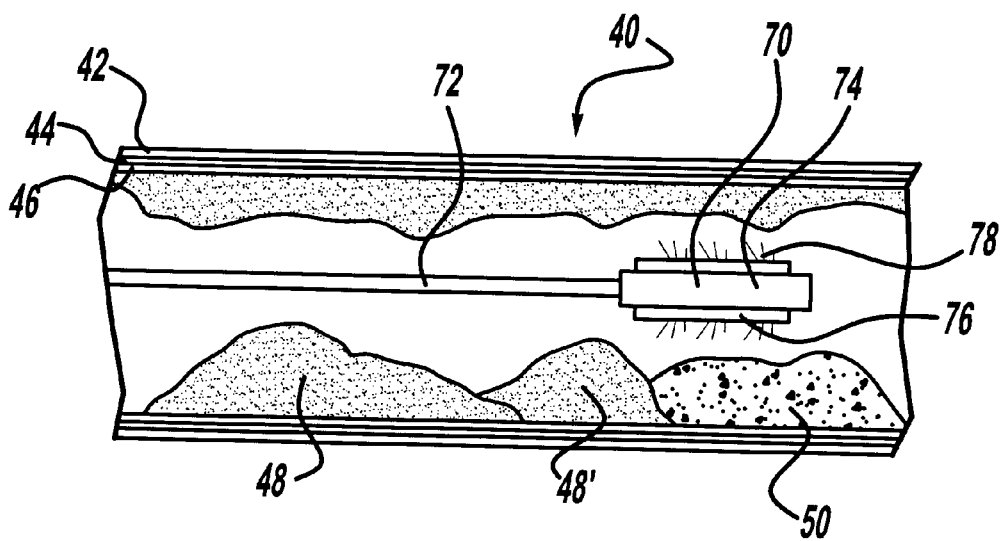
FIG. 5 is a sectional view of a blood vessel similar to that shown in FIGS. 3 and 4 but illustrating a further alternate embodiment of the catheter of the present invention.

With respect to the third possible mode of treatment, that of delivery of a metabolism-altering agent to the affected site, this may be carried out chemically or radiologically. If chemical treatment is preferred, a metabolism-altering agent such as receptor ligands, targeted nucleic acids or cell transfer agents may be delivered to the site by a combined detector-delivery apparatus fitted with outlets for allowing the outflow of the chemical agent directly to the site. Once bathed by the chemical, activity is halted or slowed. A mechanism for providing delivery of the chemical agent is illustrated in FIG. 5 which illustrates a sectional view of the blood vessel 40 which, as with FIGS. 3 and 4, includes the inactive, stable plaque deposits 48, 48' the active, unstable plaque deposit 50.

A combined treatment-sensor 70 is illustrated and includes a cable 72, a detector portion 74, and a treatment distributor 76. The distributor 76 is fitted with a plurality of fluid jets 78 which are used to allow an outflow of the treatment to bathe the surrounding area as desired.

Alternatively, a radiological agent such as iridium-188 (other agents may be applicable) may be used (along with a suitable carrier) to fill a balloon attached to the detector for radiological treatment. (While not specifically shown, such a structure would be very similar in outward appearance to the balloon-sensor 60 of FIG. 4.) As a further alternative, a metal stent may be radioactively charged to the degree necessary for proximal placement at the affected site. In either form, radiological treatment may be made directly to the active plaque to halt or slow its metabolic rate.

It is to be understood that while the method of the present invention teaches the targeting of active plaque through the use of 18-FDG, other radioactive tracers such as beta emitters (beta positive emitters, beta negative emitters) electron emitters, gamma emitters, or any combination could be substituted for 18-FDG. In addition to targeting the active plaque through the use of a radioactive agent, other biological activity of the active plaque may be used for identification. For example, a peptide or a specific radiolabelled antibody capable of targeting a receptor on the infiltrating cells could be used to differentiate between active and inactive cells.

In addition to the description of the present invention set forth above, it may be desired to combine the described apparatus with an external method of detection such as an ultrasound detector. This could also potentially assist the physician in identifying a suspicious area.

It is possible that the injection of the radiolabelled material into the bloodstream may create a substantial residual concentration in the blood itself which could marginalize the effectiveness of the described detector by making it difficult for the detector to differentiate between background radioactivity and the radioactivity of the active site. In this event, a bloodless field could be created around the area being investigated by blocking off the affected vessel proximally and distally with respect to the site and flushing out the infiltrated blood through the use of saline. Once flushed, the count could be taken to identify the active site.

Laboratory Methods

The Catheter-Probe

The positron-sensitive catheter probe consisted of a cylinder (diameter 3.0 mm, length 2 mm) of BC-408 plastic scintillator (Bicron, Newbury, Ohio) coupled through a bundle of seven fiber optic cables (Edmund Scientific Inc, Barrington, NG) to a photomultiplier tube (XP-1 91 1 1, RCA Electronics) and amplifier-analyzer (Ortec Amp-SCA, location, USA). A 0.5 mil aluminum window covered the face of the probe.

Injury Model of Atherosclerosis in Rabbits

All animal protocols were approved by the University of Michigan Committee on the Use and Care of Animals. Male New Zealand White rabbits, each 3–4 kg, received intramuscular telazol 6.0 mg/kg, rompun 2.2 mg/kg, nitrous oxide 1% for induction, and halothane maintenance after instituting mechanical ventilation. A distal femoral artery was exposed surgically (alternating sides in different animals), and a 4 F Fogarty embolectomy catheter (Baxter Healthcare Corp, Mundelein, Ill.) was inserted retrograde 5 cm, sufficient to enter the distal aorta. The balloon was inflated and withdrawn three times. The arteriotomy then was ligated and the wound sutured closed in layers. After recovery, all animals were fed Purina rabbit chow supplemented with 1.5% cholesterol and 7% peanut oil for three weeks. Serum cholesterol and triglycerides were measured.

FDG Experiments

Animals fasted at least four hours before receiving 90–180 MBq of F-I 8-deoxyglucose (FDG) intravenously. Two or four hours afterwards the animals were sacrificed with intravenous sodium pentothal 150 mg/kg. Intact injured and noninjured iliac arteries were harvested rapidly, and the peri-adventitial tissue stripped away. Arteries were incised longitudinally and the positron probe was placed in contact with the arterial intima. Duplicate or triplicate measurements were obtained along 1 cm artery segments in 60 second intervals, using two different detection thresholds. Background radiation levels were determined for each animal. Measurements were corrected for F-18 decay and for background counts. Probe measurements are reported as z-scores:

$$z\text{-score} = \frac{\text{counts-background}}{Sbg}$$

where counts, background represents probe counts for each interval recorded over tissue or air, respectively, and Sbg represents the standard deviation of background counts.

After probe measurements, specimens were divided in 1 cm segments, weighed, and placed in a gamma well counter. Specimens of brain, myocardium, kidney, spleen, liver, and blood also underwent gamma counting.

Histopathology

Arterial specimens were fixed in formalin, embedded in paraffin, and stained with hematoxylin and eosin, or Oil Red 0, for macrophages, and (x-actin stain for smooth muscle cells. Quantitative histology analysis was performed by a blinded observer. Measurement included intima:media ratios, cellularity, proportion of mononuclear cell density, smooth muscle cell density, and lipid pool area.

Statistics

Probe measurements and gamma counter measurements for each specimen are reported as counts per minute less background. Data were analyzed using SPSS for Windows version 8.0. Continuous parameters are reported as mean +/− standard deviation. Positron-probe data were grouped according to artery type, and Gamma counter data were grouped according to tissue. Multiple groups were compared using analysis of variance, with Dunnett's t test for pairwise comparisons against a single control.

Laboratory Results

Figure 6:
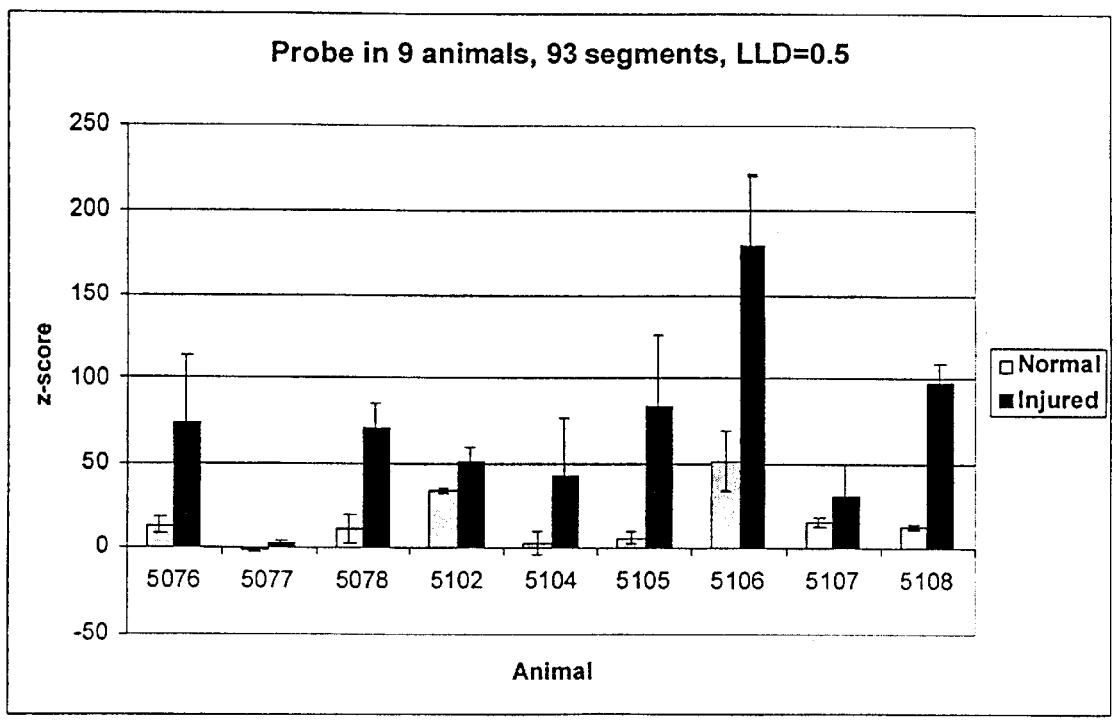
FIG. 6 is a graph of positron-sensitive probe counts of normal and injured artery segments.

FIG. 6 shows count data using the positron-sensitive probe over injured and contralateral control iliac artery segments. Mean probe z-scores were 4.8-fold higher (CI 3.4–6.3), over injury atherosclerosis compared with uninjured-normal iliac artery segments, p<0.001. At a higher detector threshold (LLD=I.O), probe z-scores remained significantly higher over injured than over normal iliac segments (Injured/Normal=3.3 (1.4–5.2), p=0.02).

Accumulation of FDG in Background Tissue

Normal iliac artery samples had a low uptake of FDG compared with injured iliac artery samples and compared with blood and nonvascular tissue. FDG accumulation was highest in "atheromatous" and reticuloendothelial tissue.

Figure 7:
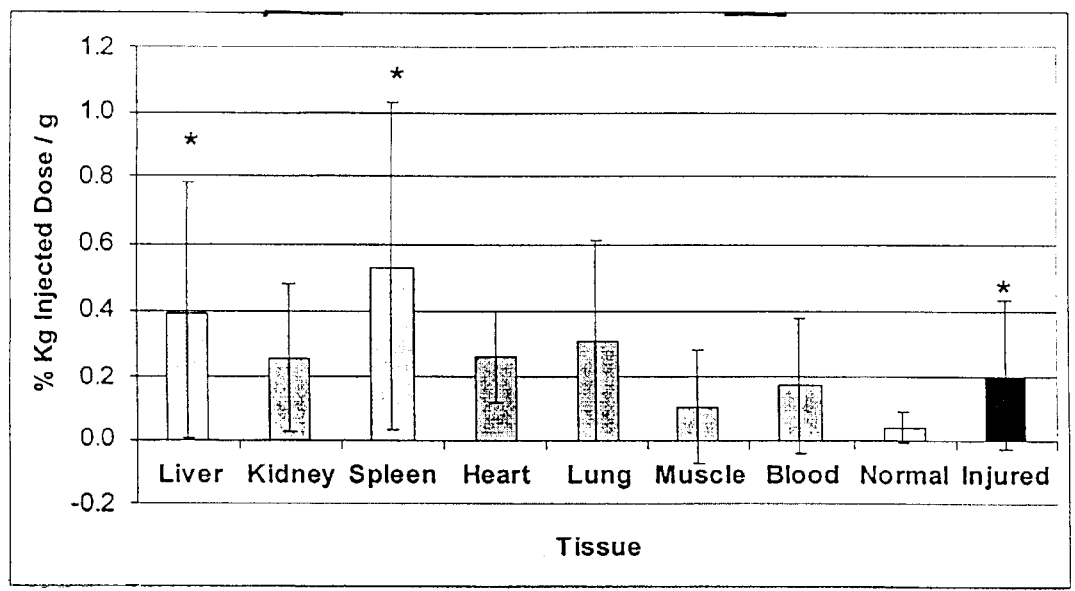
FIG. 7 is a graph of gamma counts of tissue specimens.

Gamma counting confirmed that injured artery segments accumulated more FDG per gram than did normal segments, (0.203% kg injected dose per gram versus 0.042, p<0.001, FIG. 7). Nonarterial tissue also accumulated FDG avidly, particularly reticuloendothelial tissues and blood.

Figure 8:
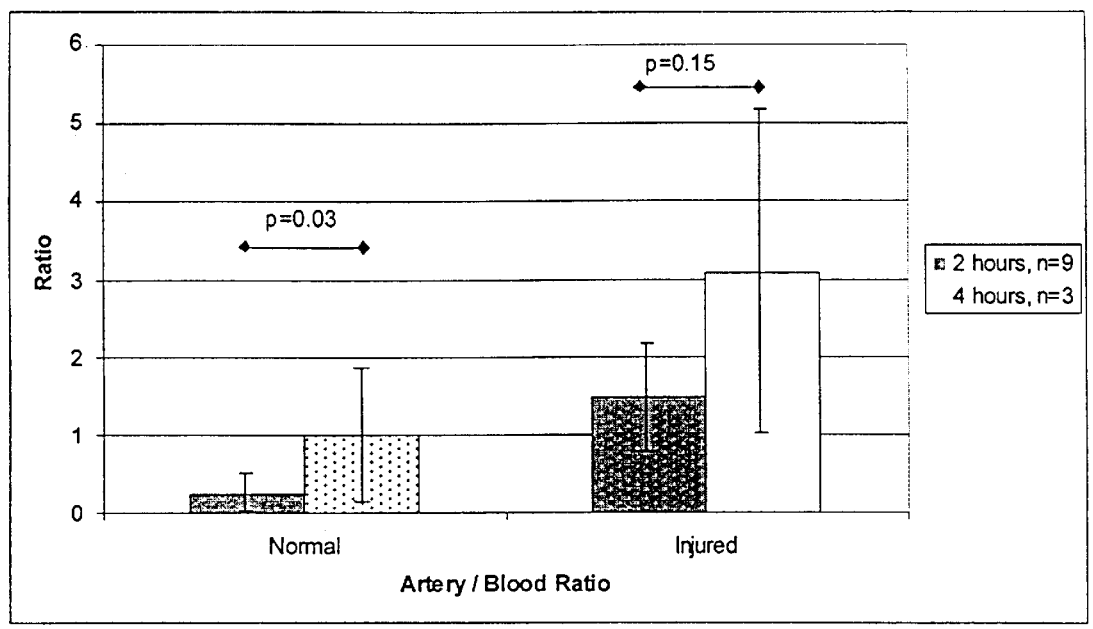
FIG. 8 shows how delayed counting reduces blood background.

Delayed tissue counting, four hours compared with two hours after animal FDG injection, further reduced blood background counts and thereby improved signal to noise ratio (FIG. 8).

Correlation with Histology

Figure 9:
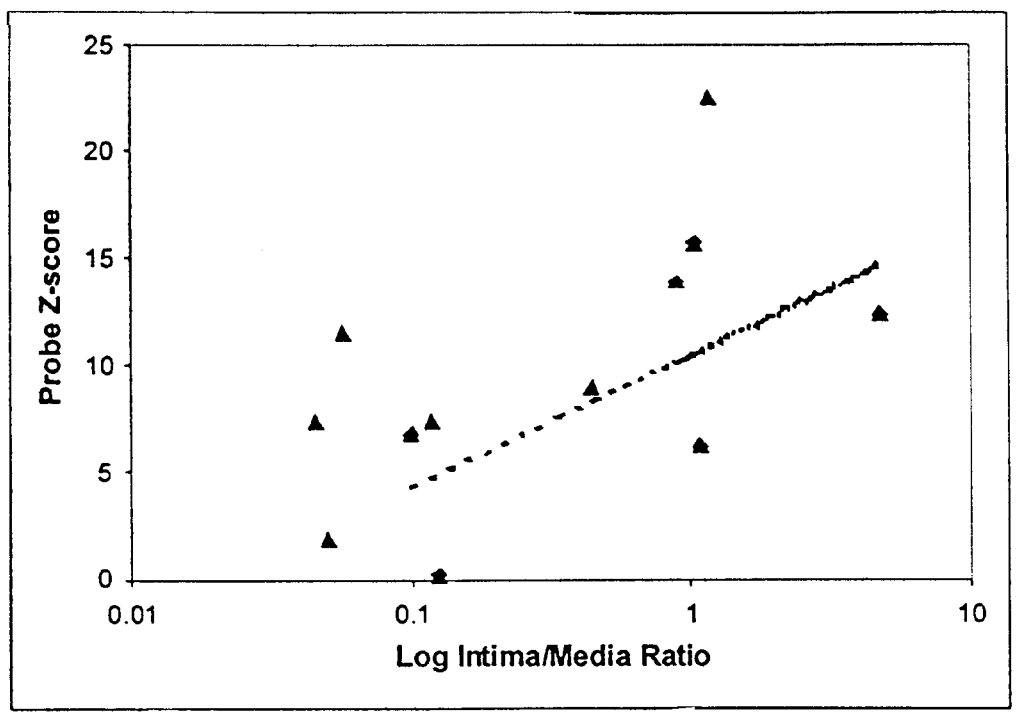
FIG. 9 shows how positron probe count correlates with intima:media ratio.

Histopathology confirmed that injured iliac artery had significantly higher intimal and medial cross-sectional area compared with uninjured artery. Injured artery also had significantly higher macrophage and smooth muscle cell density. Positron-sensitive probe counts correlated with intima:media ratio (FIG. 9).

Cholesterol was elevated. Glucose was not changed.

Discussion Of Laboratory Findings

The study demonstrated the feasibility of detecting atherosclerosis in a rabbit injury model using FDG and a novel positron-sensitive probe. Radiolabeled glucose is taken up avidly by injured arterial segments and less so by uninjured artery, and corresponds to tissue macrophage density.

Glucose uptake is one marker of a relative hypermetabolic state of atherosclerotic tissue, which is characterized in most stages by a dense cellular infiltrate of macrophages, smooth muscle cells, and lymphocytes. The data suggest the hypermetabolic state is related to this cellular infiltrate. Others using positron emission tomography, have detected intense FDG uptake in the aorta of LDL-receptor-deficient Watanabe rabbits. The hypermetabolic state is profound enough also to cause significant temperature heterogeneity. Others were able to detect atherosclerotic plaque in fresh carotid endarterectomy tissue using focal thermography. Indeed temperature elevation correlated with plaque mononuclear cell density and inversely with cap thickness.

Plaque enlargement and vulnerability to rupture may be related to several concurrent processes: an accumulation of thrombogenic extracellular lipid, a mechanical and enzymatic stress applied to a fragile overlying fibrous cap, and infiltration by inflammatory mononuclear cells which elaborate degradative enzymes and mitogens.

A catheter-based positron-sensitive probe might be used to detect a number of radiopharmaceutical agents that might provide useful information about plaque biology in vivo. Applicants chose FDG as the initial positron-emitting radiopharmaceutical because it is inexpensive and readily available. More complex agents might include monoclonal antibodies or peptide fragments to detect cell-surface markers of inflammatory activation such as HLA-DR or CD40-ligand, matrix elements including metalloproteinases or tissue factor, lipoprotein pools, or platelet deposition.

These feasibility experiments have a number of limitations. Arterial segments were examined ex vivo and thus were not subject to background activity of surrounding arterial and nonarterial tissue. However, the selected probe is sensitive to beta-particles, which penetrate only 1–2 mm of soft tissue, and relatively insensitive to annihilation gamma photons, which travel much greater distances. Surrounding tissue is expected therefore not to provide important noise. More vexing will be the problem of blood pool activity of FDG. The preliminary gamma counting data suggest that blood FDG activity is high compared to injured arterial segments. A successful catheter-based system may require transient interruption of blood flow, as with an occlusion balloon, or may require a radiopharmaceutical system that is taken up rapidly by the tissue of interest yet cleared rapidly from the bloodstream. Finally, the injury model of atherosclerosis is identical to de novo human atherosclerosis, and is characterized more by mononuclear infiltrates than by a lipid pool or vulnerable cap.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A method for use in detecting focal accumulation of radiopharmaceutical agents within an arterial lumen of a patient, the method comprising the steps of:

creating a bloodless field within the vessel of investigation by blocking off the affected vessel proximally and distally with respect to a site and flushing out a quantity of infiltrated blood;

injecting into the patient a solution containing a radioactive tracer which specifically accumulates in metabolically active plaque;

forming a miniaturized radiation detector and readout for local radioactivity imaging and detection;

inserting said radiation detector into a blood vessel of the patient;

interpreting information produced by said readout; and treating said metabolically active plaque.

2. A method for use in detecting focal accumulation of radiopharmaceutical agents within an arterial lumen of a patient, the method comprising the steps of:

injecting into the patient a solution containing a radioactive tracer which specifically accumulates in metabolically active plaque;

forming a miniaturized radiation detector and readout for local radioactivity imaging and detection;

inserting said radiation detector into a blood vessel of the patient;

characterizing the radioactivity to ascertain whether the atherosclerotic plaques as active, unstable, or vulnerable;

quantifying a concentration of said atherosclerotic plaque by comparing a ratio of abnormal-to-normal metabolic activity; and treating said metabolically active plaque according to its characterization.

3. The method of detecting of claim 2 wherein treating further comprises expanding a balloon catheter within an affected area of said blood vessel to increase an inside diameter of said blood vessel.

4. The method of detecting of claim 2 wherein treating further comprises mechanically removing said atherosclerotic plaque within an affected area of said blood vessel to reduce said atherosclerotic plaque within said blood vessel.

5. The method of detecting of claim 2 wherein treating further comprises delivering a metabolic altering agent to an affected area of said blood vessel to reduce said atherosclerotic plaque within said blood vessel.

6. A method for use in detecting focal accumulation of radiopharmaceutical agents within an arterial lumen of a patient, the method comprising the steps of:

injecting into the patient a solution containing a radioactive tracer which specifically accumulates in metabolically active plaque;

forming a miniaturized radiation detector and readout for local radioactivity imaging and detection;

inserting said radiation detector into a blood vessel of the patient;

detecting nuclear particles within the pathological tissue;

differentiating the pathological tissue of interest from any background radiation;

isolating the volume of pathological tissue of interest from the larger pool of background radioactivity;

reading the level of radioactivity along a vessel wall;

quantifying a concentration of said atherosclerotic plaque;

characterizing the radioactivity to ascertain whether the atherosclerotic plaques as active, unstable, or vulnerable; and treating said metabolically active plaque according to its characterization.

7. The method of detecting of claim 6 wherein injecting further comprises the injection of a radioactive tracer such as 18-FDG or similar radioactive tracer.

8. The method of detecting of claim 6 wherein injecting further comprises creating a bloodless field within the vessel of investigation by blocking off the affected vessel proximally and distally with respect to the site and flushing out the infiltrated blood through the use of saline.

9. The method of detecting of claim 6 wherein reading further comprises withdrawing the catheter in incremental amounts and taking a reading at each increment.

10. The method of detecting of claim 6 wherein inserting further comprises inserting said catheter to an extreme distal position from a point of epidermal insertion, said extreme distal position being the furthest location from the epidermal insertion point at which a reading will be desired.

11. The method of detecting of claim 6 wherein treating further comprises expanding a balloon catheter within an affected area of said blood vessel to increase an inside diameter of said blood vessel.

12. The method of detecting of claim 6 wherein treating further comprises mechanically removing said atherosclerotic plaque within an affected area of said blood vessel to reduce said atherosclerotic plaque within said blood vessel.

13. The method of detecting of claim 6 wherein treating further comprises delivering a metabolic altering agent to an affected area of said blood vessel to reduce said atherosclerotic plaque within said blood vessel.

14. The method of detecting of claim 6 wherein quantifying a concentration of said atherosclerotic plaque further comprises comparing a ratio of abnormal-to-normal metabolic activity.

* * * * *

UNITED STATES PATENT AND TRADEMARK OFFICE
CERTIFICATE OF CORRECTION

PATENT NO. : 6,295,680 B1 Page 1 of 1
DATED : October 2, 2001
INVENTOR(S) : Richard L. Wahl and Robert J. Lederman It is certified that error appears in the above-identified patent and that said Letters Patent is hereby corrected as shown below:

Title page,
Item [63], under Related U.S. Application Data, insert -- Provisional application No. 60/084,681, filed 05/07/1998 --.
Item [56], References Cited, under U.S. PATENT DOCUMENTS, "O'Dommell" should be -- O'Donnell --.

Column 3,
Line 22, "traceablity" should be -- trackability --.

Signed and Sealed this

Thirtieth Day of July, 2002

*Attest:*

*Attesting Officer*

JAMES E. ROGAN
*Director of the United States Patent and Trademark Office*